United States Patent [19]

Begin et al.

[11] 4,183,927

[45] Jan. 15, 1980

[54] SUBSTITUTED PHENYLTHIOALKYLAMINES AND COMPOSITIONS THEREOF

[75] Inventors: Louis E. Begin, Midland, Mich.; Robert J. Broersma, Jr., Noblesville; George D. Dickerson, Indianapolis, both of Ind.; Joseph E. Dunbar, Midland, Mich.

[73] Assignee: The Dow Chemical Company, Midland, Mich.

[21] Appl. No.: 832,848

[22] Filed: Sep. 13, 1977

Related U.S. Application Data

[63] Continuation-in-part of Ser. No. 714,949, Aug. 16, 1976, abandoned.

[51] Int. Cl.[2] .................. C07D 295/10; A61K 31/535

[52] U.S. Cl. ............................ 424/248.5; 424/248.52; 424/244; 424/267; 424/330; 544/85; 544/158; 544/159; 546/240; 260/239 B; 260/570.5 CA; 260/570.5 S; 260/239.7

[58] Field of Search ................................ 544/158, 85; 424/248.52, 248.5

[56] References Cited

FOREIGN PATENT DOCUMENTS 4612M 11/1966 France .................................. 260/247.1

OTHER PUBLICATIONS

Karaulova et al., "Chem. Abstracts," vol. 83, (1975), No. 178680y.

Wright et al., "J. Amer. Chem. Soc.," vol. 76, (1954), pp. 4396–4398.

Maier et al., "Chem. Abstracts," vol. 78, (1973), No. 72118c.

Witt et al., "Chem. Abstracts," vol. 73, (1970), No. 45111k.

*Primary Examiner*—Alan L. Rotman
*Assistant Examiner*—R. W. Ramsuer

[57] ABSTRACT

Novel substituted phenylthioalkylamines, salts and pharmaceutical compositions thereof wherein the sulfur may appear as a sulfide, sulfinyl or sulfonyl are disclosed as antithrombotic agents.

23 Claims, No Drawings

SUBSTITUTED PHENYLTHIOALKYLAMINES AND COMPOSITIONS THEREOF

CROSS REFERENCE TO RELATED APPLICATIONS

This application is a continuation-in-part of copending U.S. Application Ser. No. 714,949 filed Aug. 16, 1976 now abandoned.

BACKGROUND OF THE INVENTION

Adenosine diphosphate, hereafter called ADP, is a principle factor in the aggregation of blood platelets. Platelet aggregation in the blood stream of a mammal can lead to the formation of a thrombus. Agents which interfere with ADP-induced platelet aggregation are of use as antithrombotic drugs.

Substituted phenyl (N,N-dialkylamino)alkyl sulfides have been described in British Patent No. 718,322. Other phenyl alkyl sulfides having dialkylamino or arylamino groups attached to the alkyl are also known from the literature. See Chawla et al., J. Med Chem. 13, 480 (1970); Schuetz et al., J. Amer. Chem. Soc. 80, 162 (1958); Kim et al., J. Amer. Chem. Soc. 74, 5102 (1952); Chem. Abstracts 79:18712; and British Pat. 1,371,650. Known phenyl alkyl sulfides have displayed pharmacological properties as analgesics, anesthetics, central muscle relaxants, diuretics, and bactericides. In addition, analogs of N-[2-(4-chlorophenylthio)ethyl]-N,N-diethylamine hydrochloride have been studied as inhibitors of carotenoid biosynthesis in *Phycomyces blakesleeanus.* See Elahi, Phytochemistry 14, 133 (1975). Aminoalkyl aryl sulfides have also been described by Karaulova et al. in Khimiia Geterotsiklicheskikh Soedinenii 11, No. 6, 759–764 (1975). None of the known compounds have been reported to have an inhibitory effect on the aggregation of blood platelets.

Various (aminoalkyl thio)heterocyclic compounds are shown in the literature to be platelet aggregation inhibitors. See Elslager et al., J. Med. Chem. 15(1), 61 (1972) and Elslager et al., J. Heterocyclic Chem. 9, 1109 (1972).

SUMMARY OF THE INVENTION

The present invention relates to novel substituted phenylthio(sulfinyl or sulfonyl)alkylamines which are represented by the general formula:

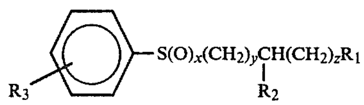

wherein:

$R_1$ represents a diloweralkylamino group of from 1 to about 4 carbon atoms such as, for example, dimethylamino, diethylamino, dipropylamino, diisopropylamino, dibutylamino, or diisobutylamino, a dicycloalkylamino group, such as, for example, dicyclohexylamino, or a cycloimino group such as, for example, piperidine, hexamethyleneimino, or morpholino;

$R_2$ represents lower alkyl of from 1 to about 2 carbon atoms, morpholino, 4-morpholinylmethyl, or hydrogen;

$R_3$ represents hydroxy, carboxy, acetamido, or acetoxy;

x is an integer of from 0 to 2;

y is an integer of from 0 to 2 with the proviso that when $R_2$ is lower alkyl or morpholino y is 1 and when $R_2$ is 4-morpholinylmethyl y is 0; and z is an integer of from 0 to 3 with the proviso that when $R_2$ is hydrogen z is 0.

Compounds represented by the above general formula have been found to be effective in the inhibition of blood platelet aggregation and are useful as antithrombotic drugs in mammals.

The invention also includes the pharmaceutically-acceptable salts of the substituted phenylthio(sulfinyl or sulfonyl)alkylamine compounds described herein. As used in the specification and claims, the term "pharmaceutically-acceptable salts" refers to non-toxic acid addition salts of the substituted phenylthio(sulfinyl or sulfonyl)alkylamine compounds, the anions of which are relatively innocuous to animals at dosages consistent with good platelet aggregation inhibition so that the beneficial effects of the free base are not vitiated by the side effects ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids, and the like.

DETAILED DESCRIPTION OF THE INVENTION

Compounds of the present invention may be prepared by reacting a corresponding substituted benzenethiol with a dialkylaminoalkyl halide, dicycloalkylaminoalkyl halide or cycloiminoalkyl halide. The reaction is usually carried out under alkaline conditions. In general, the reaction may be represented by the general formula

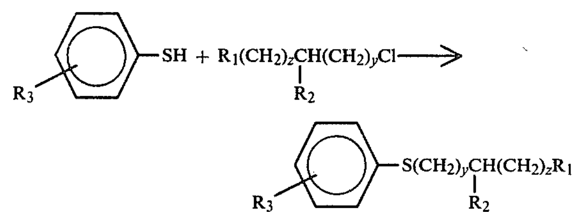

wherein z, y, $R_1$, $R_2$, and $R_3$ represent the same integers or groups as described above.

Sulfinyl and sulfonyl derivatives of the sulfides prepared above may be obtained by oxidizing the sulfur with an oxidizing agent such as hydrogen peroxide. Sulfonyl derivatives have also been prepared directly by reacting substituted benzenesulfinic acid or a sulfinate salt thereof with the aminoalkyl halide.

As noted above, compounds included within the present invention are potent inhibitors of ADP-induced platelet aggregation. It was also found that small structural changes in the compounds of the invention produced changes in potency. The most desirable substitution on the phenyl ring is hydroxy. The oxidation level of the sulfur also has an effect on the antithrombotic activity of the compounds. In general, the sulfonyl derivatives were found to be preferred for use as antithrombotic drugs. The sulfinyl and sulfide derivatives, although less active than sulfonyl, also showed satisfactory activity when used in the inhibition of ADP-induced blood platelet aggregation. Branching of the carbon chain by a lower alkyl or morpholino group between the phenyl and amino moieties in some instances also produced a marked improvement in the activity of the compound.

Compounds of the present invention having as their amine moieties dimethylamino, diethylamino, diisopropylamino, dicyclohexylamino, or piperidino while still operable as antithrombotics were found in some cases to have cardiovascular side effects which narrowed the margin of safety between the dose levels required to achieve the desired antithrombotic activity and the toxic levels at which undesirable side effects occured in the animals. For this reason, compounds having a morpholino group are preferred. It was found that compounds having the morpholino group attached to the alkyl portion gave good inhibition of ADP-induced platelet aggregation and could be administered at relatively high dosages without showing any significant toxic effects on the treated animal.

In forming the compositions of the invention, the active ingredient is incorporated in a pharmaceutical carrier. The term "pharmaceutical carrier" refers to pharmaceutical excipients and includes nutritive compositions such as a solid or liquid foodstuff. In the present specification and claims, "pharmaceutical excipient" refers to known pharmaceutical excipients which are substantially non-toxic and non-sensitizing at dosages consistent with good platelet aggregation inhibiting activity. A preferred pharmaceutical carrier is a surface active dispersing agent.

Suitable solid pharmaceutical carriers which can be employed for formulating the compositions of the invention include starch, lactose, glucose, sucrose, gelatin, microcrystalline cellulose, powdered licorice, powdered tragacanth, malt, rice flour, silica gel, magnesium stearate, magnesium carbonate, hydroxypropyl methyl cellulose, chalk and the like, and compatible mixtures thereof. In the preparation of solid compositions, the active ingredient can be triturated with a solid pharmaceutical carrier or mixtures thereof, or otherwise mechanically milled to obtain a uniform mixture. The mixtures can be compressed into tablets or filled into capsules by known procedures, or they can be employed as powders or the like. The solid compositions generally contain from about 0.02 to about 90, inclusive, percent by weight of the active ingredient.

Among the liquid pharmaceutical carriers which can be utilized are ethyl alcohol, propylene glycol, polyethylene glycols, peanut oil, corn oil, water, saline solution, glycerine and water mixtures, glucose syrup, syrup of acacia, mucilage of tragacanth and the like, and compatible mixture thereof.

The compositions can also contain the active ingredient in admixture with surface-active dispersing agents and, optionally, an inert carrier. Suitable surface-active dispersing agents include natural phosphatides such as lecithin, natural gums such as gum acacia and gum tragacanth, condensation products of ethylene oxide with fatty acids, such as polyoxyethylene stearate, condensation products of ethylene oxide with fatty alchols such as heptadecaethyleneoxycetanol and esters or partial esters of fatty acids with a hexitol or hexitol anhydride, and their condensation products with ethylene oxide, such as sorbitan monooleate, polyoxyethylene sorbitan monooleate and polyoxyethylene sorbitan monooleate. Such compositions can be in the form of emulsions, suspensions or dispersible powders or granules, and the compositions containing surface-active dispersing agents can also be in the form of tablets, capsules, or the like.

The pharmaceutical compositions described above can also contain, in addition, sweetening agents such as sugar, saccharin or the like, flavoring agents such as carmel, preservatives such as ethyl p-hydroxybenzoate, antioxidants such as ascorbic acid and suitable coloring materials.

The phenylthio(sulfinyl or sulfonyl)alkylamines compounds can also be incorporated in a foodstuff such as, for example, butter, margarine, edible oils and the like. The active compounds can also be prepared in the form of a nutritive composition in which the active ingredient is mixed with vitamins, fats, proteins or carbohydrates and the like, or mixtures thereof. Such compositions can be prepared in liquid form such as emulsions or suspensions, as well as in solid form. The nutritive compositions are adapted to be administered as the total diet. The nutritive compositions preferably contain from 0.02 to about 2 percent of the active ingredient when administered as the total diet. The compositions can contain higher concentrations of the active ingredient when administered as a supplement.

The phenylthio(sulfinyl or sulfonyl)alkylamines can also be formulated as concentrated compositions which are adapted to be diluted by admixtures with liquid or solid foodstuffs. The concentrated compositions are prepared by mechanically milling or othewise mixing the active ingredient with an inert carrier such as silica gel, soluble casein, starch or the like, or mixtures thereof. The concentrated compositions can also include additional ingredients such as vitamins, preservatives, antioxidants and flavoring agents. Such compositions contain from 5 to about 90 percent of active ingredient.

The following examples serve to further illustrate the present invention but are not to be construed as a limitation thereon.

EXAMPLE 1

Preparation of 4-(3-(4-Hydroxyphenylthio)propyl)morpholine

A mixture was prepared containing 55.5 grams (0.440 mole) of 4-hydroxybenzenethiol, 88.0 grams (0.440 mole) of 20% sodium hydroxide, and 160 ml of water. To this 72.0 grams of 4-(3-chloropropyl)morpholine was added. The reaction mixture was heated to reflux with stirring and immediately after cooled and diluted with water. The product separated out as an oil, but crystallized upon standing. Recrystallization from methylcyclohexane and ethanol gave white crystals of 4-(3-(4-hydroxyphenylthio)-propyl)morpholine having a melting point of 130.5°-131° C.

Elemental analysis showed carbon 61.9%, hydrogen 7.43%, and nitrogen 5.45% as compared to theoretical percentages of 61.62, 7.56, and 5.53 respectively.

EXAMPLE 2

4-(3-(4-Hydroxyphenylsulfinyl)propyl)morpholine p-Toluenesulfonic Acid Salt

A mixture was prepared containing 48.5 grams (0.114 mole) of 4-(3-(4-hydroxyphenylthio)propyl)morpholine toluenesulfonic acid salt and 200 ml of glacial acetic acid. To this stirred mixture 12.5 grams (0.110 mole) of 30% hydrogen peroxide was added at such a rate as to keep the temperature of the reaction mixture below 30° C. The resulting solution was stirred at room temperature for three hours after which period of time the solvent was removed by evaporation under reduced pressure. The residue was dissolved in water, and the pH was adjusted to 7.3 by the addition of dilute sodium hydroxide solution. The mixture was extracted with methylene chloride, the extract dried over anhydrous magnesium sulfate and the solvent removed by evaporation in vacuo. The crude free base was obtained as an oil. The oil was dissolved in propanol-2, and the solution was treated with p-toluenesulfonic acid in a propanol-2 solution. The crude 4-(3-(4-hydroxyphenylsulfinyl)propyl)-morpholine p-toluenesulfonic acid salt precipitated and was recrystallized from nitromethane to give a white, crystalline solid having a melting point of 167°-168° C.

Elemental analysis showed carbon 54.7%, hydrogen 6.24% and nitrogen 3.21% as compared to theoretical amounts of carbon 54.40%, hydrogen 6.16%, and nitrogen 3.17%.

EXAMPLE 3

4-(3-(4-Hydroxyphenylsulfonyl)propyl)morpholine Hydrochloride

A first solution of 19.0 grams (0.0999 mole) of p-toluenesulfonic acid monohydrate in propanol-2 was added with stirring to a second solution containing 25.0 grams (0.0987 mole) of 4-(3-(4-hydroxyphenylthio)-propyl)-morpholine and 400 ml of warm propanol-2. The p-toluenesulfonic acid salt precipitated and was suspended in 200 ml of glacial acetic acid. 30% Hydrogen peroxide (23.0 grams, 0.203 mole) was added slowly to the stirred suspension while keeping the temperature of the reaction mixture below 35° C. by means of a cooling bath. After the addition was complete the mixture was kept at 55° to 60° C. for a period of 15 hours. Excess hydrogen peroxide was destroyed by warming the reaction mixture to 95° C. The acetic acid was removed by evaporation in vacuo. The residue was dissolved in water, and the pH of the solution adjusted to the isoelectric point (about 8.0). The mixture was extracted with methylene chloride and the extract dried over anhydrous sodium sulfate. The solvent was removed by evaporation in vacuo, and the residue was dissolved in ethanol. The solution was treated with an excess of ethanolic hydrogen chloride to give 14.0 grams of 4-(3-(4-hydroxphenylsulfonyl)propyl)morpholine hydrochloride as a white crystalline solid. Following vacuum drying the melting point was found to be 197°-198° C.

Elemental analysis showed carbon 48.7%, hydrogen 6.18%, and nitrogen 4.58% as compared to theoretical values of carbon 48.51%, hydrogen, 6.26%, and nitrogen 4.35%.

EXAMPLE 4

4-(2-(4-acetamidophenylsulfonyl)ethyl)morpholine

Sodium carbonate (11.0 grams, 0.104 moles) was added to a stirred mixture of 9.96 grams (0.0500 mole) of 4-acetamidobenzenesulfinic acid, 9.30 grams (0.0500 mole) of 2-(4-morpholino)ethylchloride hydrochloride, and 100 ml of water. The reaction mixture was warmed for 1¼ hours at 65° C. At the end of this period of time the mixture was cooled, extracted with methylene chloride, and the extract dried over anhydrous magnesium sulfate. The solvent was removed by evaporation in vacuo, and the residue was crystallized from ethanol to give white crystals of 4-(2-(4-acetamidophenylsulfonyl)ethyl)morpholine having a melting point of 136°-137° C.

Elemental analysis showed carbon 53.89%, hydrogen 6.35%, and nitrogen 8.89% as compared to theoretical values of carbon 53.82%, hydrogen, 6.45%, and nitrogen 8.97%.

In addition to the compounds described in the examples above, a number of other phenylthioalkylamines were prepared using the general methods already described. The compounds were as follows:

- 4-(2-(4-hydroxyphenylthio)ethyl)morpholine, m.p. 115°-116° C.
- 4-(2- (4-hydroxyphenylsulfinyl)ethyl)morpholine, m.p. 143.5°-144.5° C.
- 4-(2-(4-hydroxyphenylsulfonyl)ethyl)morpholine, m.p. 152°-153° C.
- 4-(2-(4-acetoxyphenylsulfonyl)ethyl)morpholine, m.p. 117°-117.5° C.
- 4-(3-(4-acetamidophenylsulfonyl)propyl)morpholine, m.p. 113.5°-115° C.
- N-(3-(4-hydroxyphenylthio)propyl)dimethylamine, m.p. 80°-81° C.
- N-(3-(4-hydroxyphenylsulfonyl)propyl)dimethylamine, m.p. 165°-166° C.
- 1-(2-(4-hydroxyphenylthio)ethyl)hexamethyleneimine, m.p. 110°-110.5° C.
- 4-(2-(2-carboxyphenylthio)ethyl)morpholine hydrochloride, m.p. 213°-214° C.
- 4-(3-(4-hydroxphenylthio-2-methylpropyl)morpholine p-toluenesulfonic acid salt, m.p. 132°-133° C.
- 4-(3-(4-hydroxyphenylsulfonyl)-2-methylpropyl)morpholine hydrochloride, m.p. 253°-254° C.
- 4-((2,3-di-4-morpholinylpropyl)thio)phenol methanesulfonate (1:2), m.p. about 178° C.
- N-(3-(4-hydroxyphenlthio)propyl)diisopropylamine hydrochloride, m.p. 155°-156.5° C.
- N-(3-(4-hydroxyphenylthio)propyl)dicyclohexylamine hydrochloride, m.p. 174°-176° C.
- N-(3-(3-(4-hydroxyphenylthio)piperidine, m.p. 121.5°-122.5° C.
- N-(3-(4-hydroxyphenylsulfonyl)propyl)dicyclohexylamine hydrochloride isopropylate, m.p. 133°-135° C.
- N-(3-(4-hydroxyphenylsulfonyl)propyl)diisopropylamine hydrochloride, m.p. 175°-177° C.
- N-(3-(4-hydroxyphenylsulfinyl)propyl)diisopropylamine hydrochloride, m.p. 154°-156° C.
- 4-(3-(4-hydroxyphenylsulfonyl)propyl)morpholine, m.p. 121°-122° C.
- 4-(3-(4-hydroxyphenylsulfonyl)propyl)morpholine, p-toluenesulfonate, m.p. 155.5°-156.5° C.
- 4-(3-(4-hydroxyphenylsulfonyl)propyl)morpholine succinate (2:1), m.p. 156.5°-157.5° C.
- N-(3-(4-hydroxyphenylsulfinyl)propyl)piperidine p-toluenesulfonate, m.p. 170°-171° C.
- 4-(3-(4-hydroxyphenylthio)propyl)morpholine hydrochloride, m.p. 130°-131° C.
- 4-(3-(4-hydroxyphenylthio)propyl)morpholine p-toluenesulfonate, m.p. 126.5°-127° C.
- N-(3-(4-hydroxyphenylsulfonyl)propyl)piperidine p-toluenesulfonate, m.p. 141°-141.5° C.

The effective inhibition of ADP-induced platelet aggregation by the compounds of the present invention was demonstrated both in vitro and in vivo. The in vitro methods used the techniques described by Born, Nature 194, 927 (1962). In this procedure, platelet aggregation is initiated by ADP in platelet rich plasma obtained from rats. Quantitative platelet aggregation measurements were made with a chrono-Log Aggregometer at 37° C. The concentration of the agent inhibiting ADP-induced aggregation by 50% ($IC_{50}$) was thus determined. In general, concentration ranges for ADP varied from about 0.0625–1.0 $\mu$g/ml of platelet rich plasma.

In vivo demonstration of the effectiveness of the compounds was carried out using the procedure of Broersma, et al., Thomb. diath. Haemorrhg. 29, 201 (1973). In this procedure, platelet aggregation is studied in circulating dog blood by measurement of the pressure drop across a filter with 53 micron openings through which arterial blood flows. The compounds were administered intravenously in solutions having the pH adjusted to 7.4. The compound 4-(3-(4-hydroxyphenylsulfonyl)propyl)morpholine hydrochloride was found to be particularly active in inhibiting thrombus formation and ADP-induced platelet aggregation. The antithrombotic activity of this compound was found to be significantly different from aspirin, a recognized antithrombotic agent (see Evans et al., J. Exp. Med. 128, 877), in that it inhibits the rate of both ADP and collagen-induced platelet aggregation after intravenous administration to dogs in doses as low as 5.6 $\mu$moles/kg. Other compounds of the present invention while generally less active than 4-(3-(4-hydroxyphenylsulfonyl)-propyl)morpholine hydrochloride also are operable as antithrombotic agents.

In general, the compounds of the present invention may be administered internally to an animal in daily dosages of from 5.6 micromoles to about 400 mg of active ingredient per kilogram of body weight as platelet aggregation inhibiting agents. The compounds can be administered orally or parenterally by subcutaneous, intravenous or intraperitoneal injection or by implantation or the like, oral administration being preferred. The blood platelet aggregation inhibiting amount of the compounds of the invention to be administered to an animal, that is the amount which is effective to substantially inhibit the aggregation of blood platelets, can vary depending upon such factors as the animal treated, the particular compound administered, the period of administration, and the method of administration.

We claim:

1. A compound of the formula

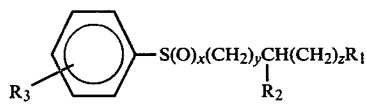

wherein:

$R_1$ is morpholino;

$R_2$ is lower alkyl of from 1 to about 2 carbon atoms, morpholino, 4-morpholinylmethyl, or hydrogen;

$R_3$ is hydroxy, or acetoxy;

x is an integer of from 0 to 2;

y is an integer of from 0 from 2 with the proviso that when $R_2$ is lower alkyl or morpholino y is 1 and when $R_2$ is 4-morpholinylmethyl y is 0;

z is an integer of from 0 to 3 with the proviso that when $R_2$ is hydrogen z is 0;

and further including the pharmaceutically-acceptable salts thereof.

2. The compound of claim 1 wherein $R_3$ is hydroxy.

3. The compound of claim 1 which is 4-(2-(4-hydroxyphenylthio)ethyl)morpholine and the pharmaceutically acceptable salts thereof.

4. The compound of claim 1 which is 4-(2-(4-hydroxyphenylsulfinyl)ethyl)morpholine and the pharmaceutically acceptable salts thereof.

5. The compound of claim 1 which is 4-(2-(4-hydroxyphenylsulfonyl)ethyl)morpholine and the pharmaceutically acceptable salts thereof.

6. The compound of claim 1 which is 4-(2-(4-acetoxyphenylsulfonyl)ethyl)morpholine and the pharmaceutically acceptable salts thereof.

7. The compound of claim 1 which is 4-(3-(4-hydroxyphenylsulfonyl)propyl)morpholine and the pharmaceutically acceptable salts thereof.

8. The compound of claim 1 which is 4-(3-(4-hydroxyphenylsulfinyl)propyl)morpholine and the pharmaceutically acceptable salts thereof.

9. The compound of claim 1 which is 4-(3-(4-hydroxyphenylthio)propyl)morpholine and the pharmaceutically acceptable salts thereof.

10. The compound of claim 1 which is 4-(3-(4-hydroxyphenylthio)-2-methylpropyl)morpholine and the pharmaceutically acceptable salts thereof.

11. The compound of claim 1 which is 4-(3-(4-hydroxyphenylsulfonyl)-2-methylpropyl)morpholine and the pharmaceutically acceptable salts thereof.

12. The compound of claim 1 which is 4-(((2,3-di-4-morpholinyl)propyl)thio)phenol.

13. A composition for inhibiting the aggregation of blood platelets in a mammal comprising a pharmaceutical carrier having incorporated therein an effective blood platelet aggregation inhibiting amount of a compound corresponding to the formula

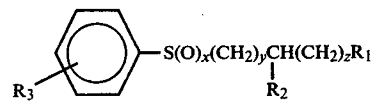

wherein:

$R_1$ is morpholino;

$R_2$ is lower alkyl of from 1 to about 2 carbon atoms, morpholino, 4-morpholinylmethyl, or hydrogen;

$R_3$ is hydroxy, or acetoxy;

x is an integer of from 0 to 2;

y is an integer of from 0 to 2 with the proviso that when $R_2$ is lower alkyl or morpholino y is 1 and when $R_2$ is 4-morpholinylmethyl y is 0;

z is an integer of from 0 to 3 with the proviso that when $R_2$ is hydrogen z is 0;

and further including the pharmaceutically-acceptable salts thereof.

14. The composition of claim 13 wherein $R_3$ is hydroxy.

15. The composition of claim 13 wherein the compound is 4-(2-(4-hydroxyphenylthio)ethyl)morpholine and the pharmaceutically acceptable salts thereof.

16. The composition of claim 13 wherein the compound is 4-(2-(4-hydroxyphenylsulfinyl)ethyl)morpholine and the pharmaceutically acceptable salts thereof.

17. The composition of claim 13 wherein the compound is 4-(2-(4-hydroxyphenlsulfonyl)ethyl)morpholine and the pharmaceutically acceptable salts thereof.

18. The composition of claim 13 wherein the compound is 4-(2-(4-acetoxyphenylsulfonyl)ethyl)morpholine and the pharmaceutically acceptable salts thereof.

19. The composition of claim 13 wherein the compound is 4-(3-(4-hydroxyphenylsulfonyl)propyl)morpholine and the pharmaceutically acceptable salts thereof.

20. The composition of claim 13 wherein the compound is 4-(3-(4-hydroxyphenylsulfinyl)propyl)morpholine and the pharmaceutically acceptable salts thereof.

21. The composition of claim 13 wherein the compound is 4-(3-(4-hydroxyphenylthio)propyl)morpholine and the pharmaceutically acceptable salts thereof.

22. The composition of claim 13 wherein the compound is 4-(3-(4-hydroxphenylthio)-2-methylpropyl)-morpholine and the pharmaceutically acceptable salts thereof.

23. The composition of claim 13 wherein the compound is 4-(3-(4-hydroxyphenylsulfonyl)-2-methylpropyl) morpholine and the pharmaceutically acceptable salts thereof.

* * * * *

UNITED STATES PATENT AND TRADEMARK OFFICE

CERTIFICATE OF CORRECTION

PATENT NO. : 4,183,927

DATED : January 15, 1980

INVENTOR(S) : Louis E. Begin, et al.

It is certified that error appears in the above-identified patent and that said Letters Patent are hereby corrected as shown below:

Column 3, line 13, "occured" should read --occurred--.

Column 3, line 52, "mixture" should read --mixtures--.

Column 3, line 60, "alchols" should read --alcohols--.

Column 4, line 26, "admixtures" should read --admixture--.

Column 4, line 28, "othewise" should read --otherwise--.

Column 5, line 46, "4-(3-(4-hydroxphenylsulfonyl)-propyl)morpho-" should read --4-(3-(4-hydroxyphenylsulfonyl)-propyl)morpho- --.

Column 6, line 29, should read --4-(3-(4-hydroxyphenylthio)-2-methylpropyl)morpholine--.

Column 6, line 35, should read --N-(3-(4-hydroxyphenylthio)propyl)diisopropylamine hy- --.

Column 6, line 39, should read --N-(3-(4-hydroxyphenylthio)propyl)piperidine,--.

Column 6, line 65, "techniques described" should read --techniques originally described--.

UNITED STATES PATENT AND TRADEMARK OFFICE

CERTIFICATE OF CORRECTION

PATENT NO. : 4,183,927

DATED : January 15, 1980

INVENTOR(S) : Louis E. Begin, et al.

It is certified that error appears in the above-identified patent and that said Letters Patent are hereby corrected as shown below:

Column 7, line 58, Claim 1, "from 2 with" should read --to 2 with--.

Column 8, line 62, Claim 17, should read --pound is 4-(2-(4-hydroxyphenylsulfonyl)ethyl)morpho- --.

Column 10, line 2, Claim 22, should read --pound is 4-(3-(4-hydroxyphenylthio)-2-methylpropyl)- --.

Signed and Sealed this

*Third* Day of *June 1980*

[SEAL]

*Attest:*

SIDNEY A. DIAMOND

*Attesting Officer* *Commissioner of Patents and Trademarks*